United States Patent [19]
Indravudh

[11] Patent Number: 5,785,681
[45] Date of Patent: Jul. 28, 1998

[54] FLOW RATE CONTROLLER FOR A MEDICATION INFUSION PUMP

[75] Inventor: Virote Indravudh, Saugus, Calif.

[73] Assignee: MiniMed Inc., Sylmar, Calif.

[21] Appl. No.: 804,629

[22] Filed: Feb. 25, 1997

[51] Int. Cl.$^6$ ............................................. A61M 31/00
[52] U.S. Cl. ............................................................ 604/65
[58] Field of Search ........................... 604/65–67, 93, 604/131, 140–141, 246–247, 890.1, 891.1; 128/DIG. 12, DIG. 13

[56] References Cited

U.S. PATENT DOCUMENTS

| | | | |
|---|---|---|---|
| 4,258,711 | 3/1981 | Tucker et al. | 128/DIG. 12 |
| 4,714,462 | 12/1987 | Didomenico | 604/67 |
| 4,931,050 | 6/1990 | Idriss | 604/891.1 |
| 5,061,242 | 10/1991 | Sampson | 604/246 |
| 5,088,983 | 2/1992 | Burke | 604/891.1 |
| 5,207,666 | 5/1993 | Idriss et al. | 604/891.1 |

Primary Examiner—Michael Buiz
Assistant Examiner—Manuel Mendez
Attorney, Agent, or Firm—Kelly Bauersfeld Lowry & Kelley, LLP.

[57] ABSTRACT

A flow rate controller is provided for regulating the flow rate of medication delivered to a patient by an implantable medication infusion pump of the constant flow type, to minimize or prevent flow rate increases attributable to fluctuations in ambient pressure. The infusion pump comprises an implantable pump housing with a pressurized medication reservoir therein for continuous flow delivery to the patient through a baseline flow path including a restrictor such as a capillary tube. The controller comprises a pressure responsive control valve for connecting a secondary restrictor such as an additional capillary tube in series with the baseline flow path, to prevent undesired increase in the medication flow rate in the event that the patient temporarily encounters a high altitude ambient pressure.

12 Claims, 1 Drawing Sheet

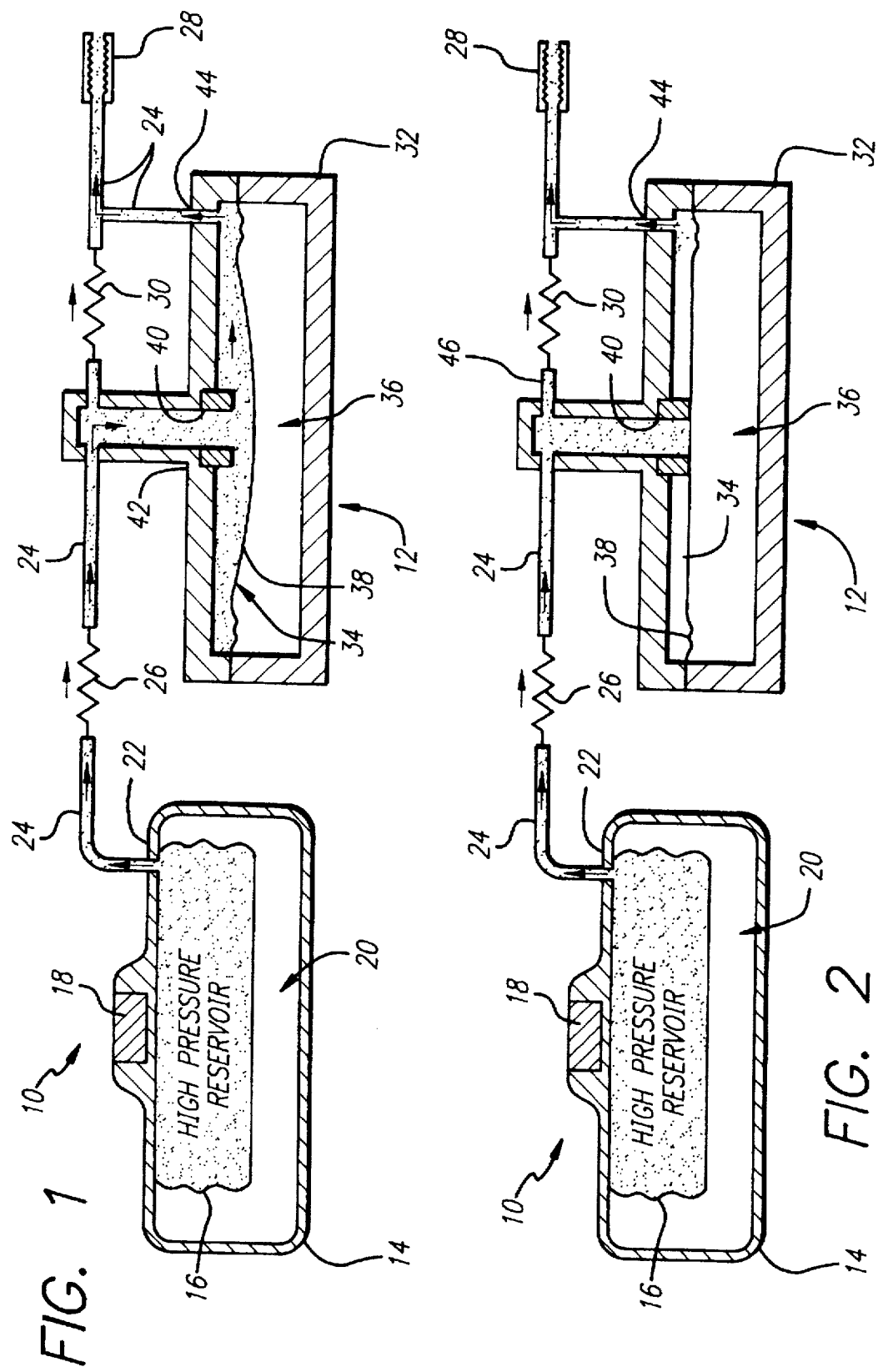

FLOW RATE CONTROLLER FOR A MEDICATION INFUSION PUMP

BACKGROUND OF THE INVENTION

This invention relates generally to improvements in medication infusion pumps of the type for implantation directly into the body of a patient, and for delivering medication to the patient at a continuous and preferably substantially constant flow rate over an extended period of time. More particularly, this invention relates to a flow rate controller for use with a medication infusion pump of the so-called constant flow type, to compensate for fluctuations in ambient pressure.

Implantable medication infusion pumps of the constant flow type are generally known in the art, for use in administering a selected medication to a patient at a substantially constant flow rate over an extended period of time. Such infusion pumps generally comprise a compact pump housing designed for direct implantation into the body of the patient. The pump housing contains an expansible medication reservoir or chamber constructed at least in part from a deformable material such as a flexible bag-type reservoir or a deformable bellows, and filled with the selected medication. The medication reservoir is subjected to a predetermined positive pressure to force the medication therein to flow through a reservoir outlet for further passage to and through a catheter to the patient. A restrictor such as a capillary tube or a suitable orifice is mounted along the outlet flow path to provide a fixed resistance to fluid flow, whereby the predetermined positive pressure applied to the medication reservoir cooperates with the known flow restriction to result in a known and substantially constant flow rate delivery of the medication to the patient. The reservoir is typically designed for periodic transcutaneous refilling via an inlet port formed on the pump housing. For one example of a constant flow implantable medication infusion pump of this general type, see commonly assigned U.S. Ser. No. 08/871,830 entitled CONSTANT FLOW MEDICATION INFUSION PUMP, filed Jun. 6, 1997.

Constant flow medication infusion pumps of the general type described above are, however, subject to at least some variation in medication flow rate delivered to the patient during certain operating conditions. More particularly, the medication flow rate is normally directly proportional to the pressure drop between the medication reservoir and the outlet end of the delivery catheter. Conversely, the flow rate is inversely proportional to the restriction presented by the outlet flow path including the known restrictor. These parameters can vary as the patient travels to a different altitude location, to result in an increase in medication flow rate. Specifically, as the patient moves to a location of lower ambient pressure, e.g., a high altitude location or during air travel in a typical commercial aircraft, the relative pressure drop between the medication reservoir and the catheter increases to result in a relatively increased medication flow rate. In some circumstances, the increased medication flow rate during this condition can be undesirable, and potentially result in an overdosage of the medication to the patient.

Accordingly, there exists a need for improvements in and to implantable medication infusion pumps of the constant flow type, to prevent or minimize medication flow rate increases attributable to the patient traveling to a high altitude pressure location. The present invention provides a relative simple and effective flow rate controller which fulfills these needs and provides further related advantages.

SUMMARY OF THE INVENTION

In accordance with the invention, an implantable medication infusion pump of the constant flow type is provided with a flow rate controller for regulating the medication flow rate to a patient in accordance with fluctuations in ambient pressure. The flow rate controller includes a pressure responsive control valve for selectively connecting a secondary restrictor such as a capillary tube in series with a baseline flow path through which medication is delivered to the patient, during a low ambient pressure condition, to maintain the actual flow rate to the patient substantially constant.

The implantable medication infusion pump comprises a compact pump housing adapted for direct implantation directly into the body of the patient. The pump housing contains a deformable medication reservoir filled with the selected medication and subjected to a predetermined positive pressure to cause the medication to flow from the reservoir through the baseline flow path including an appropriate catheter to the patient. The baseline flow path defines a known restriction to fluid flow, such as by including a primary restrictor in the form of an elongated capillary tube or the like. During normal ambient pressure conditions, e.g., ambient pressure at sea level, the known pressure applied to the medication reservoir and the known restriction defined by the baseline flow path result in a substantially constant and known flow rate of the medication to the patient. However, the pressure drop across the baseline flow path progressively increases, to progressively increase the medication flow rate, as the patient moves to a higher altitude and lower ambient pressure.

The pressure control valve of the flow rate controller is mounted along the baseline flow path at a position downstream from the primary restrictor. The control valve includes a pressure control chamber having one wall thereof defined by a resilient diaphragm positioned for opening and closing a valve port formed along the baseline flow path. The control chamber is charged with a predetermined control pressure, such as a pressure corresponding with a moderate altitude ambient pressure condition. When the patient is at a low altitude location wherein the ambient pressure at the valve port is higher than the control pressure, the diaphragm is spaced from the valve port to provide an open and substantially unrestricted pathway for medication flow to the catheter. However, when the patient travels to a higher altitude location wherein the ambient pressure at the valve port is less than the control pressure, the diaphragm moves to close the valve port and thereby divert the medication for flow through the secondary restrictor prior to passage to the catheter. The secondary restrictor is thus coupled in series with the baseline flow path and cooperates with the primary restrictor to maintain the medication flow rate substantially constant despite the high altitude location.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 1 is a somewhat diagrammatic view depicting a medication infusion pump including a flow rate controller embodying the novel features of the invention, and showing the flow rate controller in an open position for normal pump operation;

FIG. 2 is a diagrammatic view similar to FIG. 1, but depicting the flow rate controller in a closed position to divert medication flow through a secondary restrictor.

DETAILED DESCRIPTION OF THE PREFERRED EMBODIMENT

As shown in the exemplary drawings, a medication infusion pump referred to generally by the reference numeral 10 includes a flow rate controller 12 for pressure responsive regulation of the medication flow rate to a patient. The flow rate controller 12 is designed to compensate for fluctuations in the ambient pressure to maintain a substantially constant actual medication flow rate to the patient.

The medication infusion pump 10 is shown in FIGS. 1 and 2 to have a generally conventional construction adapted for direct implantation into the body of a patient, and to administer a selected medication to the patient on a continuous and desirably substantially constant flow rate over an extended period of time. In this regard, the illustrative pump 10 comprises a compact pump housing 14 formed from a suitable biocompatible material to include an internal medication reservoir or chamber 16 of a deformable or expansible construction. An inlet port 18 is mounted on the pump housing to permit transcutaneous filling and refilling of the medication reservoir 16, all in a manner known to persons skilled in the art.

The infusion pump 10 also includes a propellant chamber 20 within the pump housing 14 for applying a predetermined positive pressure to the medication within the reservoir 16. More particularly, the propellant chamber 20 comprises a volume within the pump housing filled with a selected fluid propellant such as a freon compound having a vapor pressure to apply a selected and predetermined positive pressure to the medication within the reservoir. The fluid propellant is selected to volumetrically expand and contract as the medication reservoir 16 is gradually emptied and subsequently refilled, respectively, in a manner maintaining a substantially constant pressure applied to the medication.

Although FIGS. 1 and 2 show the infusion pump 10 in a schematic form, it will be recognized and understood that the particular construction of the medication reservoir 16 and the propellant chamber 20 within the implantable pump housing 14 may take different forms. For example, in a preferred configuration, the medication reservoir 16 is constructed to occupy the substantial volume of the housing interior, and the propellant chamber 20 is provided as a sealed flexible bag positioned directly within the medication reservoir, all as shown and described in commonly assigned U.S. Ser. No. 08/871,830, entitled CONSTANT FLOW MEDICATION INFUSION PUMP, filed Jun. 6, 1997, and incorporated by reference herein. Alternately, the medication reservoir 16 may be provided as an expansible bellows chamber, such as that shown and described in U.S. Pat. No. 3,951,147, which is also incorporated by reference herein.

The medication under pressure within the medication reservoir 16 is forced to flow through an outlet port 22, for flow further through a baseline flow path 24 to the patient. This baseline flow path 24 defines a known and predetermined restriction to fluid flow, so that the flow rate therethrough in response to the constant pressure applied by the pressure chamber 20 will be substantially constant. In this regard, the predetermined flow restriction is normally obtained by providing a suitable primary flow restrictor 26 such as an elongated capillary tube along the length of the flow path 24. As shown, the medication flows through the capillary tube 26 through the flow rate controller 12 of the present invention as will be described, and further to the patient via an appropriate catheter 28 or the like.

The flow rate controller 12 is mounted along the baseline flow path 24 at a location downstream from the capillary tube 26, and comprises a pressure control valve which functions to allow substantially uninterrupted flow of the medication therethrough during normal operating conditions. That is, when the patient is located in a normal ambient pressure environment, for example, an ambient pressure corresponding with or approximately equal to atmospheric pressure at sea level, the flow rate controller 12 permits substantially unrestricted flow of the medication from the capillary tube 26 to the catheter 28. However, when the patient moves to or otherwise encounters a lower ambient pressure, the controller 12 diverts the medication for flow through a secondary restrictor 30 which may be provided in the form of an additional capillary tube.

More specifically, the flow rate of the medication from the reservoir 16 to the patient is a function of the pressure drop along the baseline flow path 24 between the reservoir 16 and an outlet end of the catheter 28. At a normal ambient pressure condition, at or near atmospheric pressure at sea level, the pressure drop is the difference between the pressure applied by the pressure chamber 20 and the local ambient pressure. However, if the patient travels to or encounters a reduced local ambient pressure, such as by traveling to a higher altitude location or in the course of an airplane flight, the pressure drop along the baseline flow path 24 increases to result in an increase in the flow rate of the medication to the patient. The flow rate controller 12 of the present invention compensates for the increased medication flow rate which would otherwise occur during this condition by connecting the secondary restrictor 30 in series with the primary restrictor 26 to retard the flow rate substantially to the design constant flow desired.

The controller 12 comprises a valve housing 32 having a resilient diaphragm 34 subdividing the valve housing 32 into a pressure control chamber 36 and a flow chamber 38. The control chamber 36 is charged with a gas to a predetermined pressure associated with a mid or moderate altitude location, such as a pressure of about negative 2 psi corresponding with ambient pressure normally encountered at an altitude of about 4,000 feet above sea level. The flow chamber 38 is coupled via an inlet valve port 40 in-line with the baseline flow path 24 at the downstream side of the primary restrictor or capillary tube 26, wherein this valve port 40 includes a resilient valve seat 42 for engagement with the diaphragm 34. During normal operating conditions, with the ambient pressure higher than the pressure within the control chamber 36, the differential pressure across the diaphragm 34 causes the diaphragm to retract from the valve seat 42 to permit unobstructed medication flow through the valve port 40. The medication passes from the valve port through the flow chamber 38 and further through an outlet port 44 coupled to the catheter 28. This baseline flow path 24 bypasses the secondary restrictor 30 which, during normal operating conditions, provides sufficient resistance to fluid flow so that substantially all of the medication passes through the controller flow chamber 38 to the catheter 28.

When the patient encounters a reduced ambient pressure associated with an altitude higher than a predetermined reference or threshold as defined by the control pressure within the control chamber 36, the diaphragm 34 responds to the pressure differential thereacross to seat against and close the valve seat 42. When this occurs, as shown in FIG. 2, the medication is forced to flow in bypass relation to the pressure control valve through a short bypass conduit 46 which includes the secondary restrictor 30. The bypass conduit 46 connects the medication flow from the downstream side of the primary restrictor 26, through the secondary restrictor 30 and directly to the catheter 28, thereby adding the additional flow resistance defined by the secondary restrictor 30 in series with the flow resistance defined by the primary restrictor 26. As a result, as long as the higher altitude pressure condition in maintained, the flow rate controller 12 effectively increases the fluid flow resistance encountered by the medication to maintain the actual medication flow rate substantially at the original constant design flow rate. When the patient returns to a lower altitude location, as reflected by a local pressure that is higher than the pressure within the control chamber 36, the diaphragm 34 re-opens the valve seat 42 and medication flow through the original baseline flow path 24 is resumed.

The flow rate controller 12 of the present invention thus provides a relatively simple yet highly effective device for use with an implantable medication infusion pump 10, to maintain the actual medication flow rate substantially constant, notwithstanding fluctuations in the local ambient pressure. The controller 12 monitors the pressure of the medication at the downstream side of the primary restrictor 26, and responds when that pressure is less that a predetermined reference level to increase the fluid flow resistance of the pathway to the patient. The controller thus safeguards the patient against potential excess dosage of the medication, while enabling the patient to travel to high altitude locations and/or travel on aircraft without concern for improper medication dosage rate attributable to altitude variations. Although the invention is depicted in the exemplary drawings in schematic form, persons skilled in the art will recognize that the controller 12 can be incorporated directly into the housing of the infusion pump substantially without increasing the overall size of the pump.

A variety of further modifications and improvements to the invention will be apparent to those skilled in the art. Accordingly, no limitation on the invention is intended by way of the foregoing description and accompanying drawings, except as set forth in the appended claims.

What is claimed is:

1. In a medication infusion pump having a medication reservoir with a selected medication therein subjected to a predetermined positive pressure, and means forming a baseline flow path including a primary restrictor for passage of the medication from the medication reservoir to a patient, the improvement comprising:

a flow rate controller including pressure control means for detecting an increased pressure drop along the baseline flow path at a location downstream from the primary restrictor, and further including means for connecting a secondary restrictor in series with the primary restrictor when said detected increased pressure drop exceeds a predetermined threshold.

2. The improvement of claim 1 wherein said pressure control means comprises a pressure control valve including a valve housing having an internal resilient diaphragm subdividing said valve housing into a pressure control chamber and a flow chamber, said pressure control chamber being charged to a predetermined reference pressure, and said flow chamber being coupled in-line with the baseline flow path downstream from the primary restrictor, said diaphragm being movable between a first position spaced from a valve port formed on said valve housing to permit medication flow through said flow chamber when the pressure within said flow chamber is greater than said reference pressure, and a second position closing said valve port to prevent medication flow through said flow chamber when the pressure within said flow chamber is less than said reference pressure, said secondary restrictor being mounted along a bypass conduit connected to said baseline flow path to bypass said pressure control valve.

3. The improvement of claim 1 wherein said primary restrictor is a capillary tube.

4. The improvement of claim 3 wherein said secondary restrictor is a capillary tube.

5. The improvement of claim 1 wherein said secondary restrictor is a capillary tube.

6. A flow rate controller for a medication infusion pump having a selected medication contained within a deformable medication reservoir under a predetermined positive pressure for substantially continuous delivery thereof from the medication reservoir through a baseline flow path including a primary flow restrictor to a patient, said flow rate controller comprising:

a pressure control valve including means for monitoring the pressure along the baseline flow path at a location downstream from the primary flow restrictor; and a bypass conduit including a secondary flow restrictor;

said pressure control valve further including means for connecting said bypass conduit in series with the primary flow restrictor when the monitored pressure is less than a predetermined reference pressure.

7. The flow rate controller of claim 6 wherein said pressure control valve comprises a valve housing having an internal resilient diaphragm subdividing said valve housing into a pressure control chamber and a flow chamber, said pressure control chamber being charged to said predetermined reference pressure, and said flow chamber being coupled in-line with the baseline flow path downstream from the primary flow restrictor, said diaphragm being movable between a first position spaced from a valve port formed on said valve housing to permit medication flow through said flow chamber when the pressure within said flow chamber is greater than said reference pressure, and a second position closing said valve port to prevent medication flow through said flow chamber when the pressure within said flow chamber is less than said reference pressure, said secondary flow restrictor being mounted along a bypass conduit connected to said baseline flow path to bypass said pressure control valve.

8. The flow rate controller of claim 6 wherein said primary flow restrictor is a capillary tube.

9. The flow rate controller of claim 8 wherein said secondary flow restrictor is a capillary tube.

10. The flow rate controller of claim 6 wherein said secondary flow restrictor is a capillary tube.

11. A flow rate controller for a medication infusion pump having a selected medication contained within a deformable medication reservoir under a predetermined positive pressure for substantially continuous delivery thereof from the medication reservoir through a baseline flow path including a primary flow restrictor to a patient, said flow rate controller comprising:

a pressure control valve including means for monitoring the pressure along the baseline flow path at a location downstream from the primary flow restrictor; and means for adjusting the restriction to fluid flow from the medication reservoir to the patient in response to changes in the monitored pressure.

12. The flow rate controller of claim 11 wherein said adjusting means comprises means for increasing the fluid flow restriction from the medication reservoir to the patient in response to decrease in the monitored pressure.

* * * * *